United States Patent [19]
Sadowski et al.

[11] Patent Number: 5,769,138
[45] Date of Patent: Jun. 23, 1998

[54] NOZZLE AND ADAPTER FOR LOADING MEDICAMENT INTO AN INJECTOR

[75] Inventors: Peter L. Sadowski, Woodbury; Sheldon Nelson, New Hope, both of Minn.; David Schiff, Highland Park, N.J.; Walter Stoeckmann, Mahopac, N.Y.

[73] Assignee: Medi-Ject Corporation, Minneapolis, Minn.

[21] Appl. No.: 625,881

[22] Filed: Apr. 1, 1996

[51] Int. Cl.$^6$ .................................................. B65B 1/04
[52] U.S. Cl. ........................... 141/329; 141/25; 141/27; 141/384; 604/414
[58] Field of Search ................. 141/25, 27, 329, 141/330, 384, 385, 386; 604/68, 69, 70, 71, 72, 411, 414; 285/360, 361

[56] References Cited

U.S. PATENT DOCUMENTS

| | | |
|---|---|---|
| 2,450,527 | 10/1948 | Smith et al. .................. 285/361 |
| 2,547,099 | 4/1951 | Smoot . |
| 2,699,166 | 1/1955 | Dickinson, Jr. et al. . |
| 2,754,818 | 7/1956 | Scherer . |
| 2,816,543 | 12/1957 | Venditty et al. . |
| 3,057,349 | 10/1962 | Ismach . |
| 3,115,133 | 12/1963 | Morando . |
| 3,131,692 | 5/1964 | Love . |
| 3,292,622 | 12/1966 | Banker . |
| 3,343,538 | 9/1967 | Morley . |
| 3,399,759 | 9/1968 | Love . |
| 3,419,007 | 12/1968 | Love . |
| 3,526,225 | 9/1970 | Hayamamachi . |
| 3,659,587 | 5/1972 | Baldwin . |
| 3,688,765 | 9/1972 | Gasaway . |
| 3,827,601 | 8/1974 | Magrath et al. . |
| 3,908,651 | 9/1975 | Fudge . |
| 3,938,520 | 2/1976 | Scislowicz et al. . |
| 3,945,379 | 3/1976 | Pritz et al. . |
| 3,945,383 | 3/1976 | Bennett et al. . |
| 4,089,334 | 5/1978 | Schwebel et al. . |
| 4,328,802 | 5/1982 | Curley et al. . |
| 4,373,559 | 2/1983 | Mowles et al. ................ 141/329 |
| 4,421,508 | 12/1983 | Cohen . |
| 4,447,225 | 5/1984 | Taff et al. . |
| 4,505,709 | 3/1985 | Froning et al. . |
| 4,507,113 | 3/1985 | Dunlap . |
| 4,561,856 | 12/1985 | Cochran . |
| 4,588,403 | 5/1986 | Weiss et al. . |
| 4,619,651 | 10/1986 | Kopfer et al. . |
| 4,623,332 | 11/1986 | Lindmayer et al. . |
| 4,662,878 | 5/1987 | Lindmayer . |
| 4,675,020 | 6/1987 | McPhee . |

(List continued on next page.)

FOREIGN PATENT DOCUMENTS

| | | |
|---|---|---|
| 2028870 | 5/1991 | Canada . |
| 959397 | 6/1964 | United Kingdom . |
| WO 96/21482 | 7/1996 | WIPO . |

*Primary Examiner*—Henry J. Recla
*Assistant Examiner*—Steven O. Douglas
*Attorney, Agent, or Firm*—Pennie & Edmonds LLP

[57] ABSTRACT

An injector nozzle which has a body defining a chamber. A portion of the body has an orifice which communicates with the chamber for allowing fluid to enter into or exit from the chamber. The nozzle body includes at least one depression which is configured and dimensioned to cooperatively engage a tab member of an associated component for coupling thereto. The depression is also configured and dimensioned to positively lock the body to the associated component. The body portion which contains the depression is spaced proximally from the orifice. Also, an adapter for coupling the nozzle to a fluid container. The adapter includes a tubular member having first and second ends and a wall therebetween. The wall includes a passageway therethrough with the first end being dimensioned and configured to cooperatively engage the nozzle. The orifice of the nozzle generally aligns with the wall passageway for fluid communication therebetween. The second end of the adapter is configured and dimensioned to cooperatively engage a fluid container. These devices can be used in combination to provide a system for filling an injector with medicament.

22 Claims, 7 Drawing Sheets

U.S. PATENT DOCUMENTS

| | | |
|---|---|---|
| 4,680,027 | 7/1987 | Parsons et al. . |
| 4,768,568 | 9/1988 | Fournier et al. . |
| 4,790,824 | 12/1988 | Morrow et al. . |
| 4,834,149 | 5/1989 | Fournier et al. . |
| 4,883,483 | 11/1989 | Lindmayer . |
| 4,913,699 | 4/1990 | Parsons ................................. 604/68 |
| 4,989,905 | 2/1991 | Rajecki . |
| 5,024,656 | 6/1991 | Gasaway et al. . |
| 5,062,830 | 11/1991 | Dunlap . |
| 5,085,332 | 2/1992 | Gettig et al. . |
| 5,116,313 | 5/1992 | McGregor . |
| 5,165,560 | 11/1992 | Ennis, III et al. . |
| 5,193,517 | 3/1993 | Taylor et al. . |
| 5,209,362 | 5/1993 | Lutzker . |
| 5,279,576 | 1/1994 | Loo et al. . |
| 5,292,308 | 3/1994 | Ryan . |
| 5,356,380 | 10/1994 | Hoekwater et al. . |
| 5,454,409 | 10/1995 | McAffer et al. . |
| 5,480,381 | 1/1996 | Weston . |
| 5,569,189 | 10/1996 | Parsons ................................. 604/68 |
| 5,599,302 | 2/1997 | Lilley et al. ............................ 604/68 |

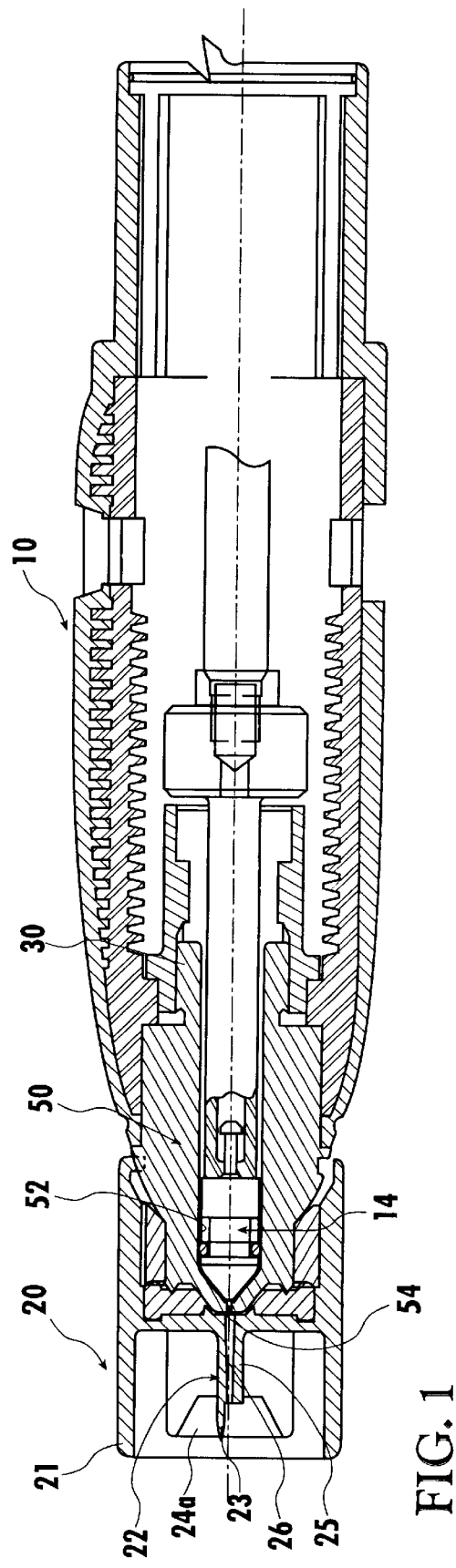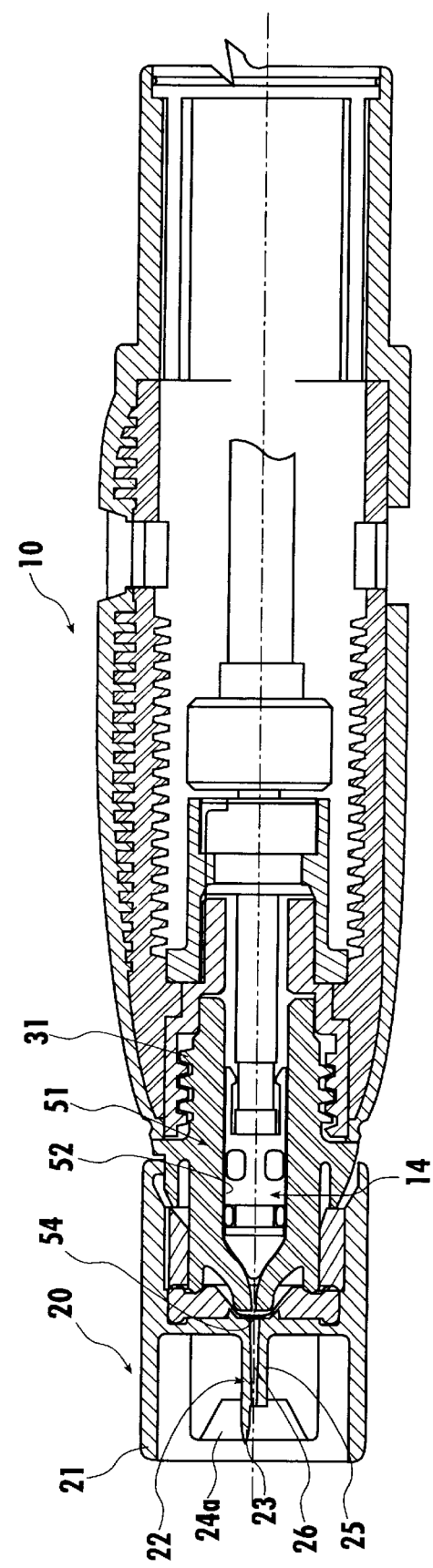

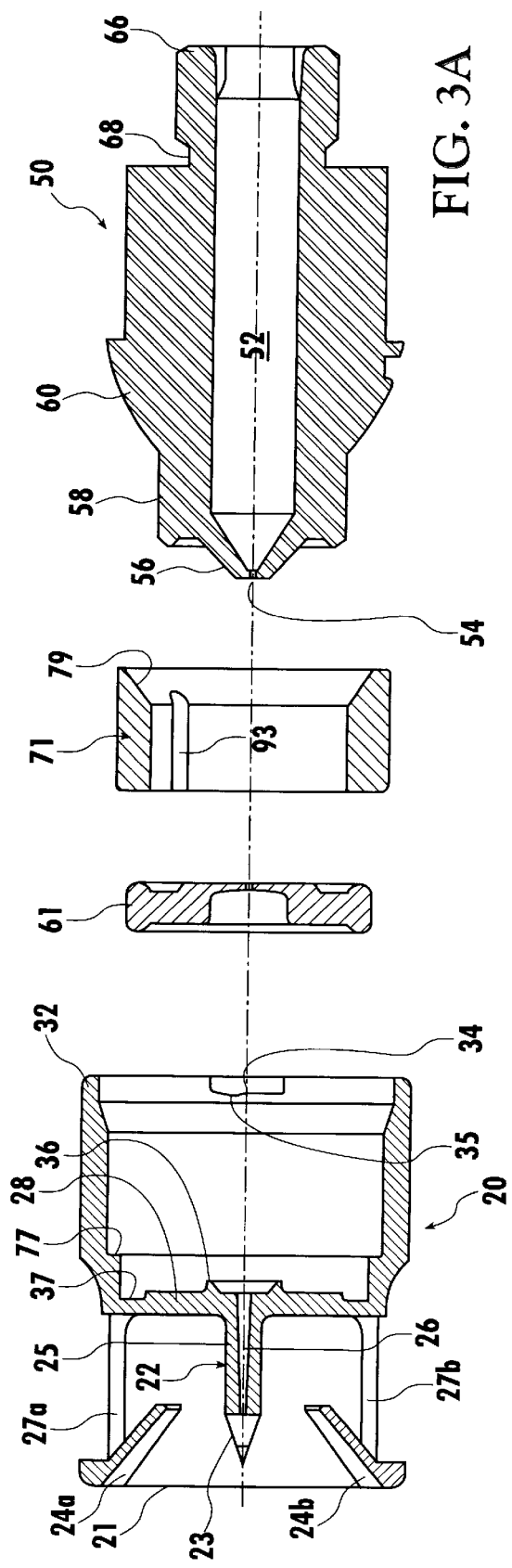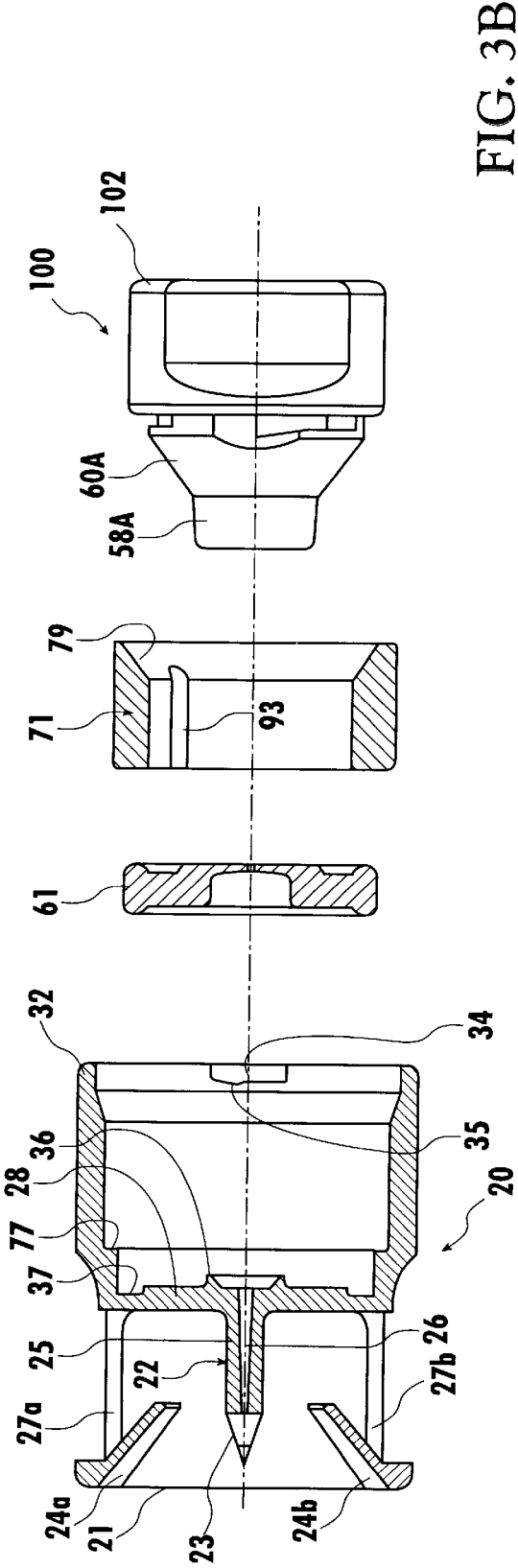

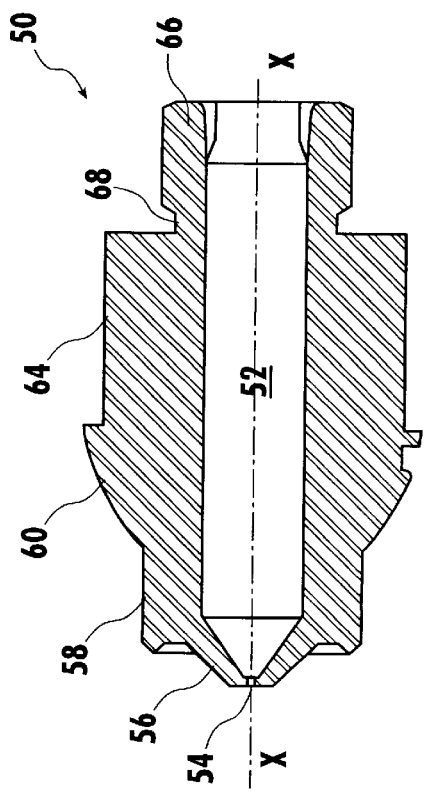
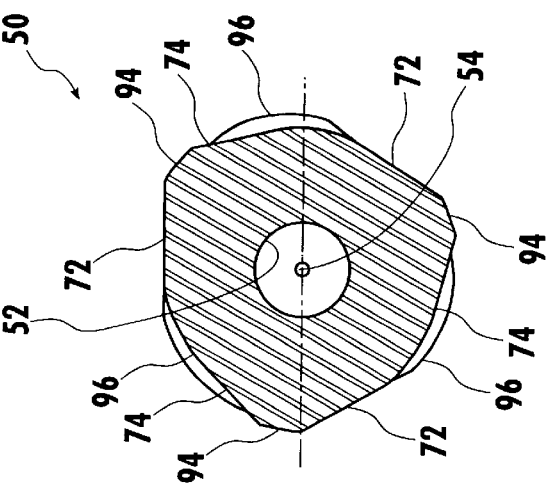
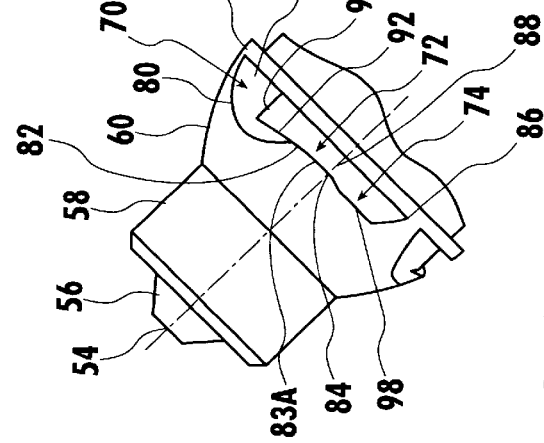
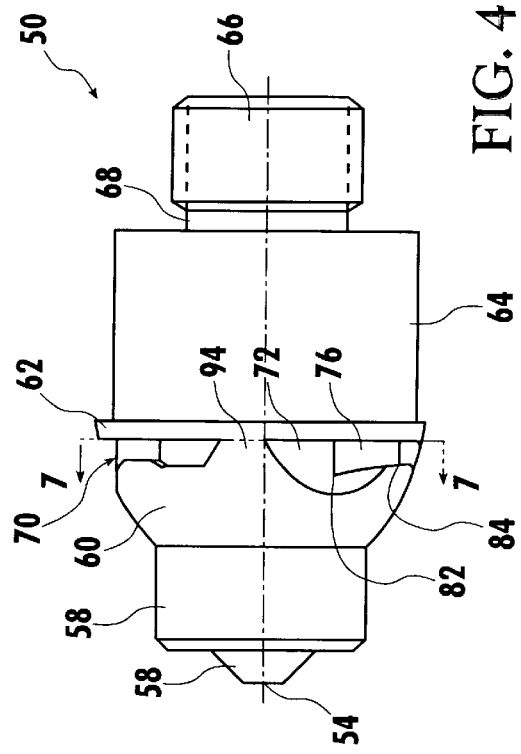
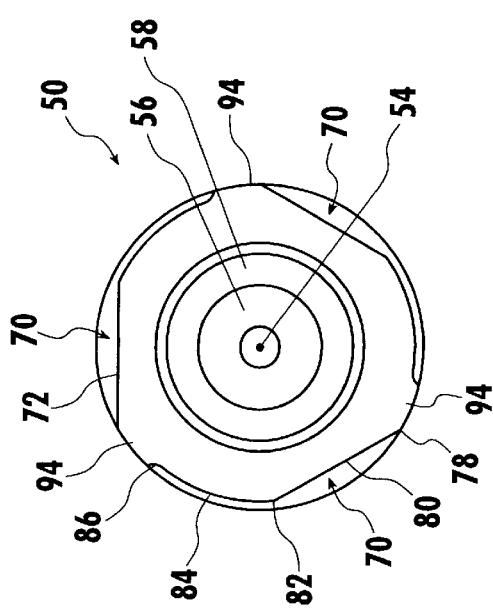

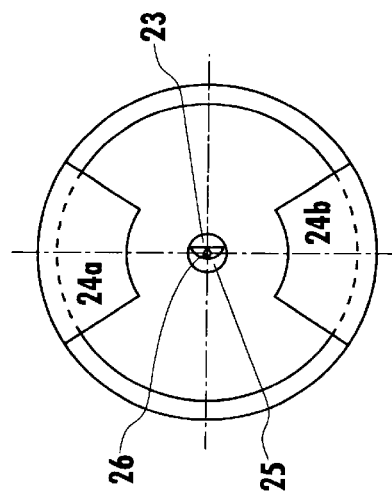
FIG. 13
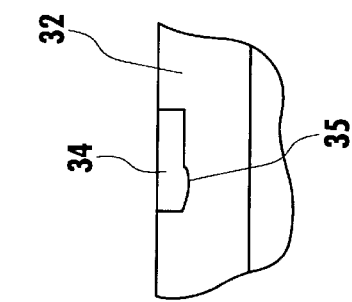
FIG. 16
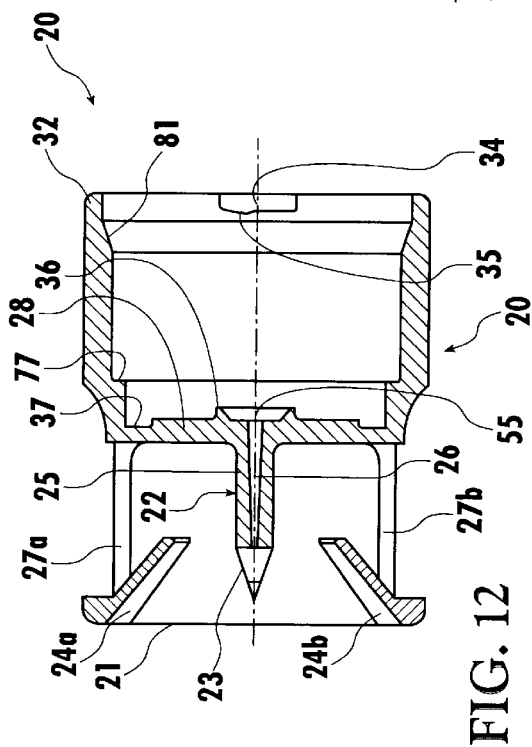
FIG. 12
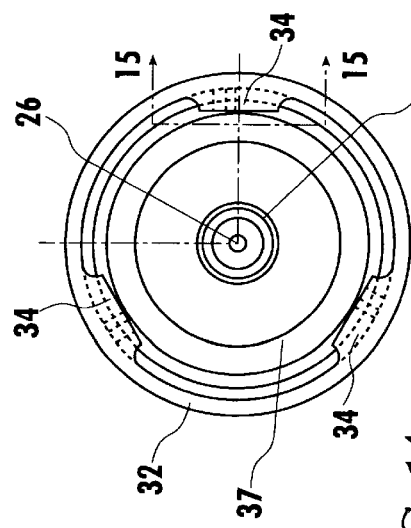
FIG. 14
FIG. 15

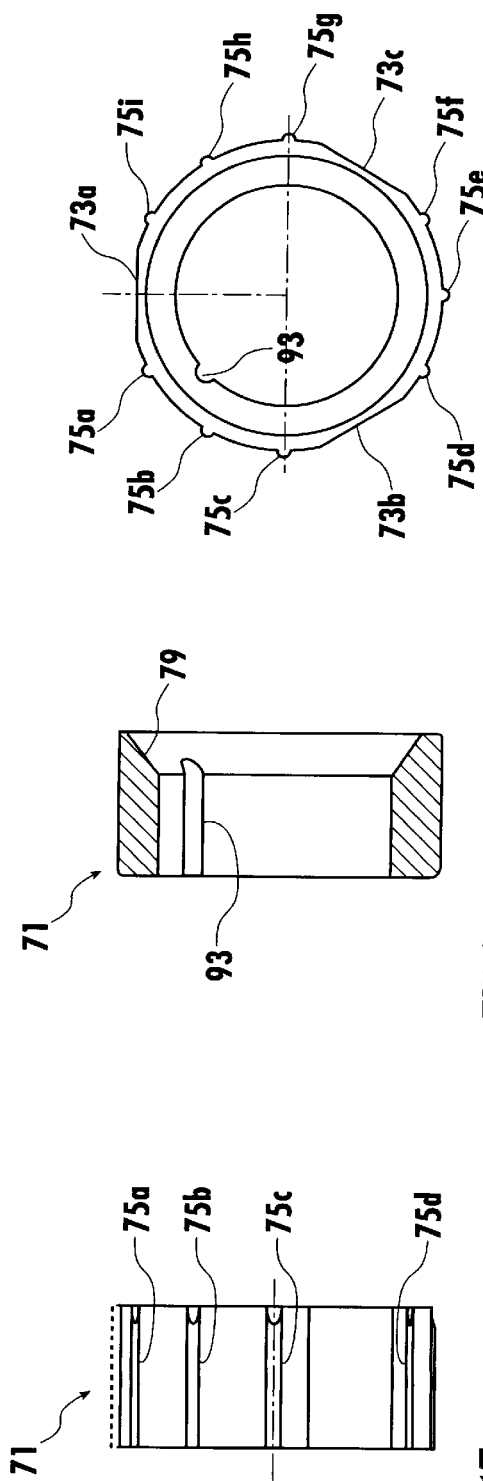
FIG. 17
FIG. 18
FIG. 19
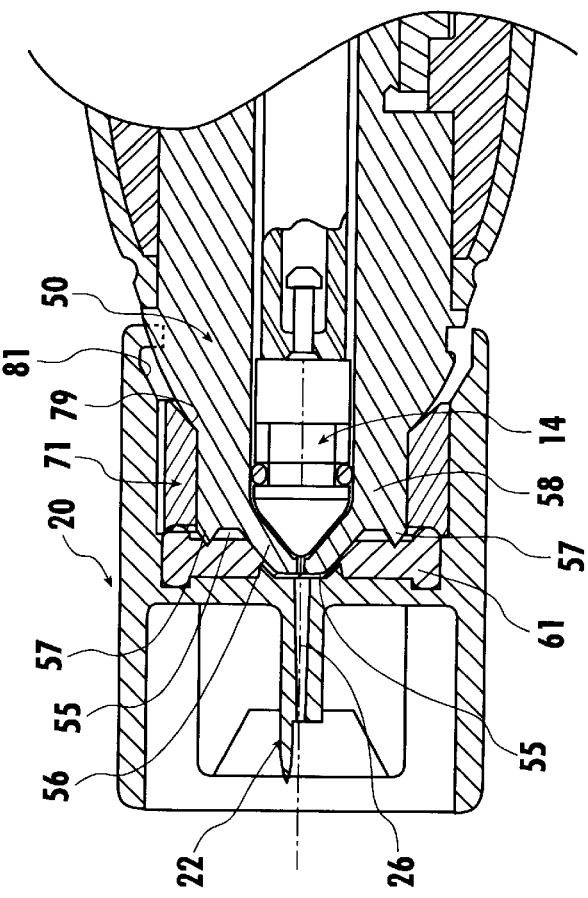
FIG. 20

NOZZLE AND ADAPTER FOR LOADING MEDICAMENT INTO AN INJECTOR

FIELD OF THE INVENTION

This invention relates generally to an adapter for use with a needleless fluid injection apparatus. More particularly, the present invention relates to an adapter which is connected to a container and a nozzle which is coupled with the adapter to cooperate with the container.

BACKGROUND OF THE INVENTION

Needleless hypodermic injection devices have been known and used in the past. These devices typically use spring or compressed gas driven plungers to accelerate a fluid at a velocity sufficient to pierce the skin and enter the underlying tissues.

Since at least the 1980s, the use of needleless injectors has become more desirable due to concerns over the spread of AIDS, hepatitis and other viral diseases caused by the possibility of accidental needle "sticks" from the conventional syringe and needle. Needleless injectors remove apprehensions of healthcare workers and are superior in eliminating accidental disease transmission.

A number of different needleless injectors are known including U.S. Pat. No. 5,062,830 to Dunlap, U.S. Pat. No. 4,790,824 to Morrow et al., U.S. Pat. No. 4,623,332 to Lindmayer et al., U.S. Pat. No. 4,421,508 to Cohen, U.S. Pat. No. 4,089,334 to Schwebel et al., U.S. Pat. No. 3,688,765 to Gasaway, U.S. Pat. No. 3,115,133 to Morando, U.S. Pat. No. 2,816,543 to Venditty, et al., and U.S. Pat. No. 2,754,818 to Scherer. These injectors typically include a nozzle member which is secured to the end of an injector body. The nozzle includes a medication holding chamber and a piston. The chamber has an orifice formed in one end thereof through which a jet of medication is forced out of the chamber using the piston actuated by some type of energy source.

In order to fill the chamber with medicament, medicament may be withdrawn from a supply vial into the chamber in order to load the injector. When the nozzle is attached to a supply vial and the piston of the injector is retracted, the resulting vacuum created causes the medicament to be withdrawn from the vial and to flow through the orifice to fill the chamber.

In order to facilitate the loading of medicament into the chamber, an adapter may be used. U.S. Pat. No. 4,507,113 to Dunlap describes an adapter design which can be used on different vials by removing a first vial and replacing it onto a second vial. An adapter of this type, being reusable, increases the risk of contamination through dirt entering the adapter openings and through small amounts of the medicament remaining within the adapter after loading and being transferred to other medicament vials. Therefore, it is desirable to provide a disposable adapter which cannot be reused, thereby preventing unwanted contamination.

Another problem found in the prior art is that prior art adapters do not efficiently remove air from the passageways disposed in the adapter between the vial and the injector. For instance, in U.S. Pat. No. 4,507,113, an air pocket will remain in the fluid passageway of the adapter after the adapter has been installed on a medicament vial and the nozzle of an injector has been installed onto the adapter. The air in this pocket will be drawn into the chamber during the charging thereof. Therefore, it is desirable to provide an improved design where the potential for air to enter the chamber of the nozzle is minimized.

SUMMARY OF THE INVENTION

A first embodiment of the present invention relates to an injector nozzle which has a body defining a chamber. A portion of the body has an orifice which communicates with the chamber for allowing fluid to enter into or exit from the chamber. The nozzle body includes at least one depression which is configured and dimensioned to cooperatively engage a tab member of an associated component for coupling thereto. The depression is also configured and dimensioned to positively lock the body to the associated component. The body portion which contains the depression is spaced proximally from the orifice.

It is preferable to include at least two depressions on the nozzle body which are uniformly disposed with respect to the orifice. Each depression can include an entry portion and a seating portion which are positioned in spaced relation by an intermediate portion.

The body portion of the nozzle may be generally cylindrical and includes a conical tip which surrounds the orifice, a cylindrical collar which surrounds the conical tip, a flange portion which has a greater circumference than the collar, and a transition portion which connects the collar to the flange portion. The transition portion preferably includes at least one depression and has a transverse cross section of generally increasing size from the cylindrical collar to the flange portion. The nozzle body may also have a proximal portion which includes engagement means for selectively coupling the nozzle to the injector.

The present invention also relates to an adapter for coupling the nozzle to a fluid container. The adapter includes a tubular member having first and second ends and a wall therebetween. The wall includes a passageway therethrough with the first end being dimensioned and configured to cooperatively engage the nozzle. The orifice of the nozzle generally aligns with the wall passageway for fluid communication therebetween. The second end of the adapter is configured and dimensioned to cooperatively engage a fluid container.

Preferably, the adapter also includes a membrane which is positioned between the wall and the first end of the tubular member. The membrane includes a generally centrally disposed aperture to facilitate fluid communication between the nozzle orifice and the wall passageway. A rib may also protrude from the wall and extend toward the first end of the tubular member for receiving an injector nozzle tip. The surface defined by the rib and the wall probably has a shape generally conforming to the nozzle tip so that the membrane seals the nozzle orifice to the wall passageway.

The adapter may also include a membrane retainer which has an annular configuration disposed within the first end of the tubular member for retaining the membrane adjacent to the wall. Also, the second end of the tubular member may also include inwardly extending frangible arm portions for engaging the fluid container and a spike which contains a fluid passage therein extending from the wall toward the second end of the tubular member for penetrating a sealing member of the fluid container.

Another embodiment of the invention relates to a system for transferring fluid from a fluid container to an injector device. This system includes an injector nozzle having a body defining a chamber, with a portion of the body having an orifice communicating with the chamber for allowing fluid to enter into or exit from the chamber. The body portion can have at least one depression configured and dimensioned to cooperatively engage with a tab member of an associated component for coupling thereto. Preferably, the depression is further configured and dimensioned to positively lock the body portion to the associated component.

The system also includes an adapter for coupling the nozzle to a fluid container, the adapter comprising a tubular member having first and second ends and a wall therebetween. As above, the wall includes a passageway therethrough with the first end being configured and dimensioned to cooperatively engage with the injector nozzle such that the nozzle orifice generally aligns with the wall passageway for fluid communication therebetween. In addition, the second end is advantageously configured and dimensioned to cooperatively engage with the fluid container.

In this system, the body portion of the nozzle contains at least two depressions which are uniformly disposed with respect to the orifice and the first end of the adapter contains at least two inwardly extending tab portions uniformly disposed therealong for engaging the depressions. The nozzle may include a conical tip which surrounds the orifice, a cylindrical collar surrounding the tip, a flange portion having a greater circumference than the collar, and a transition portion connecting the collar to the flange portion, wherein the transition portion includes the at least one depression, while the adapter includes a flexible membrane positioned between the wall and the first end of the tubular member.

The membrane may have a generally centrally disposed aperture to facilitate fluid communication between the nozzle orifice and the wall passageway, while the wall has a rib protruding from the wall and extending toward the first end of the tubular member for receiving the injector nozzle tip. A preferred flexible membrane includes an inner portion and an outer portion, with the inner portion including a generally centrally disposed aperture and having a first thickness and being dimensioned and configured for receiving the conical tip of the nozzle, while the outer portion has a second thickness which is greater than the first thickness. With this construction, the surface defined by the rib and the wall has a shape generally conforming to the nozzle tip so that the membrane seals the nozzle orifice to the wall passageway.

The adapter may further include a membrane retainer having a generally annular configuration disposed within the first end of the tubular member for retaining the membrane adjacent the wall and the collar member of the nozzle contacts the membrane and engages the inner surface of the retainer to align the nozzle orifice with the wall passageway with the membrane acting as a seal to prevent air from entering the nozzle orifice.

Also, the system may include a cap having a body for coupling to the adapter when the nozzle is removed therefrom. This cap generally defines a first body portion which is configured and dimensioned to couple with the first end of the adapter to block the transmission of fluid through the wall passageway. The first body portion of the cap includes at least one groove configured and dimensioned to cooperatively engage with the tab member of the adapter, and a second body portion includes an extending member for seating the cap within the first end of the adapter and for removing the cap therefrom.

As above, the nozzle body can have a proximal portion which includes engagement means for selectively coupling the nozzle to an injector.

BRIEF DESCRIPTION OF THE DRAWINGS

Preferred features of the present invention are disclosed in the accompanying drawings, wherein similar reference characters denote similar elements throughout the several views, and wherein:

FIG. 1 is a cross-sectional view of a needleless injector showing one embodiment of the nozzle of the present invention and the adapter of the present invention installed on the injector;

FIG. 2 is a cross-sectional view of a needleless injector showing another embodiment of the nozzle of the present invention and adapter of the present invention installed on the injector;

FIG. 3A is an exploded view of an adapter and a nozzle incorporating the designs of the present invention;

FIG. 3B is an exploded view of an adapter and a cap incorporating the designs of the present invention;

FIG. 4 is an elevated view of one embodiment of the nozzle of the present invention;

FIG. 5 is a cross-sectional view of one embodiment of the nozzle of the present invention;

FIG. 6 is a distal end view of the nozzle of the present invention;

FIG. 7 is an elevated view of the tip portion of the nozzle of the present invention shown at a rotated angle relative to the description of FIG. 4;

FIG. 8 is a cross-sectional view of the nozzle taken along line 7—7 of FIG. 4 showing the configuration of the depressions on the nozzle for receiving the adapter;

FIG. 12 is a cross-sectional view of the adapter of the present invention in a view rotated relative to FIG. 10.

FIG. 13 is a distal end view of the adapter of the present invention;

FIG. 14 is a proximal end view of the adapter of the present invention;

FIG. 15 is a cross-sectional view taken along line 15—15 of FIG. 14 showing the configuration of the tab of the present invention;

FIG. 16 is a cross-sectional view of the flexible membrane of the adapter;

FIG. 17 is an elevated side view of the membrane retainer of the adapter of the present invention;

FIG. 18 is a cross-sectional view of the membrane retainer of the adapter;

FIG. 19 is a proximal end view of the membrane retainer of the adapter;

FIG. 20 is a cross-sectional view of the present invention showing the nozzle installed in the adapter;

DETAILED DESCRIPTION OF THE PREFERRED EMBODIMENTS

Figure 10:
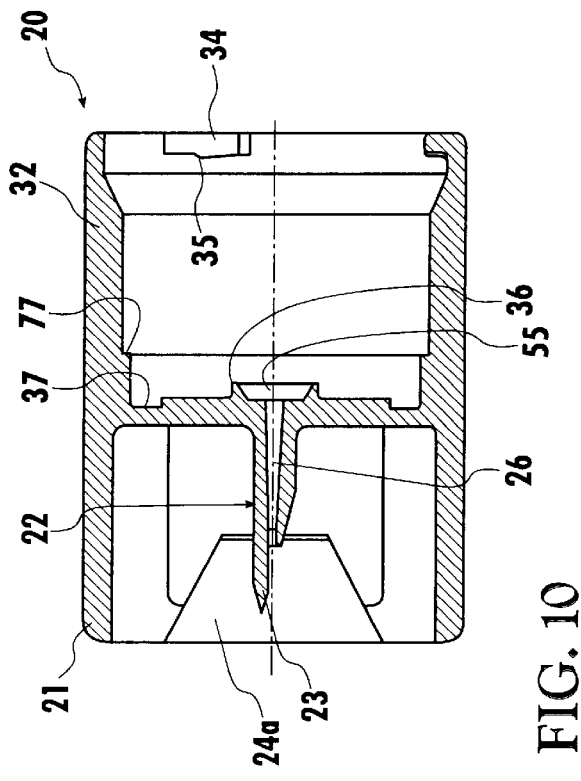
FIG. 10 is a cross-sectional view of the adapter of the present invention.

Referring to FIG. 1, a typical needleless injector is shown with one embodiment of the nozzle and adapter of the present invention installed thereon. The other components of the needleless injector 10 are generally known, e.g. from U.S. Pat. No. 5,599,302 filed Jan. 9, 1995, the content of which is expressly incorporated herein by reference thereto.

As used in this application, the term distal shall designate the end or direction toward the front of the injector 10. The term proximal shall designate the end or direction toward the rear of the injector. The term longitudinal designates an axis connecting the nozzle 50 to the injector 10, and the term transverse designates a direction substantially perpendicular to the longitudinal direction including arcs along the surface of injector 10, adapter 20, or nozzle 50.

As shown in FIGS. 1 and 2, the injector can include nozzle 50 or 51 attached to the distal end and cooperating with adapter 20. As is known by those of ordinary skill in the art, the injector 10 includes a plunger mechanism 14 which is initially positioned at the forward end of nozzle 50. To introduce a liquid medicament into the chamber 52 of the injector nozzle 50 for administration to a subject, plunger mechanism 14 is withdrawn thus allowing liquid medicament to enter into nozzle chamber 52 through nozzle orifice 54.

To facilitate the introduction of the liquid medicament in a safe and sanitary manner, adapter 20 is utilized. Adapter 20 includes spike 22 which is capable of penetrating a generally soft rubber stopper of a container of liquid medicament. Adapter 20 also includes frangible arm portions 24A, 24B which engage the shoulder of the medicament container, which is not shown but is known, e.g., from U.S. Pat. No. 4,507,113. The proximal end of adapter 20 is attached to the end of nozzle 50, 51 to place nozzle orifice 54 in proximity with the tubular channel 26 of spike 22 of adapter 20 which communicates with the liquid medicament in the container. Thus, withdrawal of plunger mechanism 14 enables chamber 52 of nozzles 50 or 51 to be filled with a liquid medicament.

FIG. 1 illustrates a stainless steel nozzle 50 which is reusable. Thus, when a medicament such as insulin is to be repeatedly administered to a subject, an injector device with stainless steel nozzle 50 can be used for such administration and can be filled each time through the use of adapter 20. This reusable nozzle 50 has a generally cylindrical configuration with the rearwardmost portion containing threads 30 for attachment to a threaded portion of the injector 10. The threads of nozzle 50 are also shown in FIG. 5 as 66.

An alternate embodiment is shown in FIG. 2, wherein a disposable plastic nozzle 51 is illustrated. This nozzle 51 has the same configuration and dimensions on the distal end as that of nozzle 50 so that it can be connected to adapter 20 in the same manner. However, due to the differences in mechanical properties of plastic material compared to stainless steel, the connection of the nozzle 51 to the injector 10 is achieved using significantly larger threads 31 on the proximal end of the nozzle for mating with similarly dimensioned and configured threads on the internal body of the injector 10.

Referring now to FIG. 3A, an exploded view of the adapter 20 and its relation to nozzle 50 is illustrated. As explained above, the distal end of nozzles 50 and 51 are identical so that the same connection can be made to the adapter 20 with either nozzle. In addition, a cap 100 is shown in FIG. 3B for sealing adapter 20 when not in use with the nozzle and injector. Cap 100 has the same or a similar configuration on its distal end as that of nozzles 50 and 51 for proper engagement with adapter 20.

Adapter 20 is made of plastic and is configured in the shape of a generally tubular member. The distal end 21 of this tubular member includes a pair of frangible arm portions 24a, 24b for engaging the neck of a fluid medicament container. As also shown in FIGS. 12 and 13, arm portions 24a, 24b are curved and extend inwardly towards spike 22. These arm portions are frangibly joined to the distal end 21 of the adapter 20 so that a secure connection can be made to the medicament container, which connection cannot be broken without damaging or breaking arm portions 24a, 24b. To contribute to the frangible nature of arm portions 24a, 24b, the distal end 21 of adapter 20 includes window 27A, 27B as shown in FIGS. 3 and 12. Thus, when adapter 20 is secured to a medicament container, it cannot be removed and reused. This avoids contamination from the multiple use of adapter 20 on different medicament containers.

When adapter 20 is attached to medicament bottle, spike 22 penetrates through the sealing member of the bottle, which is normally a relatively soft rubber stopper. Spike 22 is configured to have a pointed tip 23 as best shown in FIGS. 1, 2, 3A, 3B and 10–12, and a wider base portion 25 which includes a generally central channel 26 that allows passage of fluid from the medicament container towards the injector nozzle 50, 51.

The distal end 21 of adapter 20 ends at a wall 28 which is generally centrally oriented in adapter 20. Spike 22 extends away from wall 28 towards distal end of the adapter 20, wherein channel 26 extends through the base 25 of spike 22 and through wall 28. To take advantage of capillary action, channel 26 has a smaller cross-sectional area near the tip 23 of spike 22 and a slightly larger diameter when passing through wall 28.

Adapter 20 also has proximal end 32 which includes at least one tab 34 for engaging corresponding depressions on nozzle 50 or 51, or cap 100. As shown in FIGS. 3A, 3B, 12 and 15, tab 34 includes a bump 35 which is intended to engage the wall of a corresponding depression 70 for locking engagement therewith as described below in the description of FIGS. 4–8. In this respect, the configuration of the distal portion of tab 34 is configured and dimensioned to allow the bump 35 to slide along the wall of the corresponding depression 70 of the nozzle 50, 51 or depression 70A of cap 100 for engagement therewith. Although one tab 34 is illustrated in these Figs., it is advantageous to use a plurality of such tabs and corresponding depressions to maintain a secure engagement between adapter 20 and nozzle 50, 51 or cap 100. The most preferred arrangement is the use of three tabs as shown in FIG. 14 with corresponding depressions so that the nozzle 50, 51 can be locked into adapter 20 in the appropriate orientation with the nozzle orifice 54 directly adjacent to channel 26 of spike 22.

Adapter 20 also includes a novel arrangement for preventing air or contaminants from entering into nozzle chamber 52. On the proximal side of wall 28 is included a circular rib 36 which includes a substantially straight outer wall and an angled inner wall for defining a cup 55 which receives the tip 56 of nozzle 50, 51. Wall 28 also includes a groove 37 which receives the end of a flexible membrane 61 as shown in FIG. 16. As shown in FIGS. 3A, 3B and 16, membrane 61 includes an outer ring 63, an intermediate ring 65, an inner ring 67, a central ring 69 and an aperture 95. The thickness of central ring 69 is much less than that of the other rings of the membrane so that central ring 69 can either span the cup 55 formed by rib 36 or can be pressed into the base of the cup 55 by the nozzle tip 56. Intermediate ring 65 is made thinner than outer ring 63 and inner ring 67 so that it can partially flex to allow central ring 69 to deform as noted above. The outer ring 63 allows membrane 61 to be seated in groove 37 of wall 28.

As shown in FIGS. 3A, 3B and 17–19, a membrane retainer 71 is used to hold membrane 61 in position against the proximal side of wall 28. Retainer 71 is made of plastic and is configured in a generally cylindrical shape. As shown in FIG. 19, the outer surface of retainer 71 includes flats 73A, 73B, 73C which are configured to provide clearance between the retainer 71 and tabs 34 so that retainer 71 can be inserted into the open proximal end 32 of adapter 20.

Retainer 71 includes a plurality of external ribs 75A, 75B, 75C, 75D, etc. which engage the inner wall of proximal end 32 of adapter 20 for secure engagement therewith. Retainer 71 can be inserted into proximal end 32 of adapter 20 until it engages shoulder 77 which places the distal end of the retainer 71 securely against the proximal end of flexible membrane 61.

The inner diameter of retainer 71 includes two features which are extremely useful in the operation of the adapter 20 of the present invention. The proximal internal end of retainer 71 includes an angled surface 79 which cooperates with angled surface 81 of proximal end 32 of adapter 20 to form a surface which conforms to the outer surface of nozzle 50 as illustrated, for example, in FIG. 20. It is not critical that curved surfaces 79, 81 actually contact the exterior surface of nozzle 50, 51 but merely that they provide clearance so that the curved expanding surface 60 of the nozzle 50, 51 can be received within adapter 20.

Another feature of retainer 71 is the provision of an internal groove 93 which allows nozzle 50, 51 to be inserted into the proximal end of adapter 20 without creating a pressure buildup in front of the nozzle orifice 54. Groove 93 provides a passage for the exit of air which would otherwise be trapped between nozzle 50, 51 and the wall of adapter 20. FIG. 20 illustrates nozzle 50 in operative position in adapter 20 with the nozzle tip deforming central ring 69 of membrane 61 against the base of the cup 55 formed by wall 28 and rib 36. In this arrangement, the nozzle orifice 54, the membrane orifice 95 and the channel 26 of spike 22 are all in alignment such that fluid which is withdrawn from the medicament container will pass only into the nozzle chamber 52. The central ring 69 of membrane 61 is flattened between the nozzle tip 56 and the rib 36 of wall 28 so as to provide a sealing function which prevents air or other contamination from passing from the inner area of proximal end 32 of adapter 20 into the nozzle orifice 54 and nozzle chamber 52.

Figure 9:
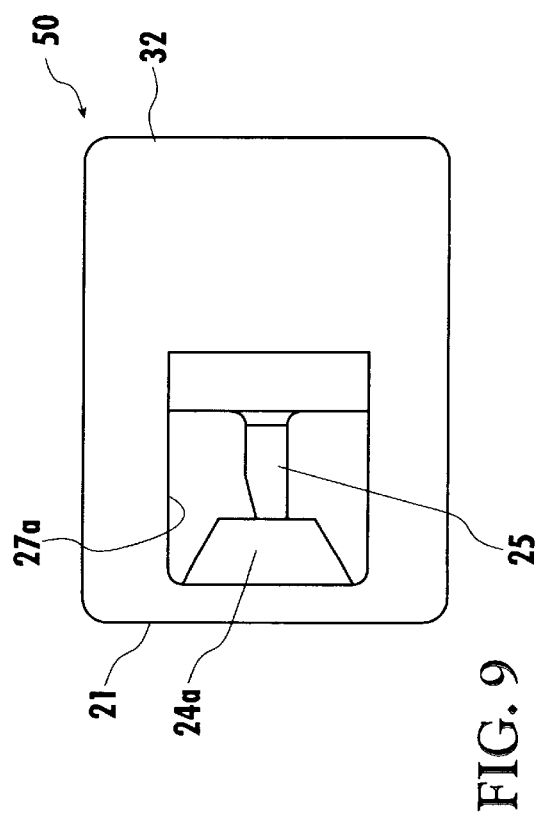
FIG. 9 is a side elevated view of the adapter of the present invention.
Figure 11:
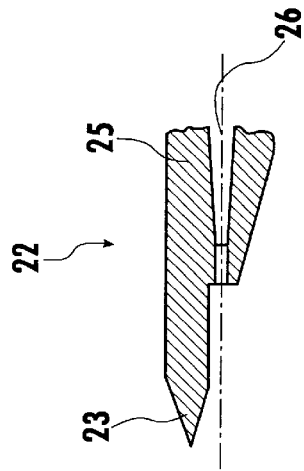
FIG. 11 is a detail view of the spike shown in FIG. 10.
Figure 21A:
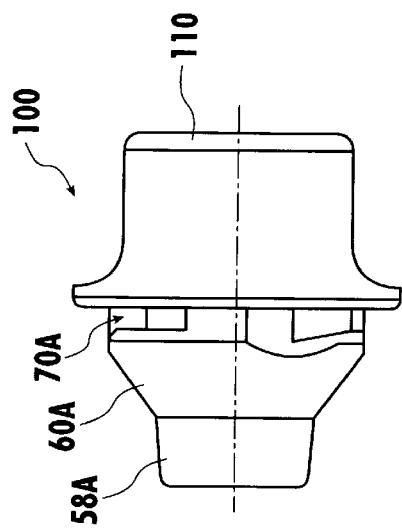
FIG. 21A is a side elevational view of the cap of the present invention.
Figure 21B:
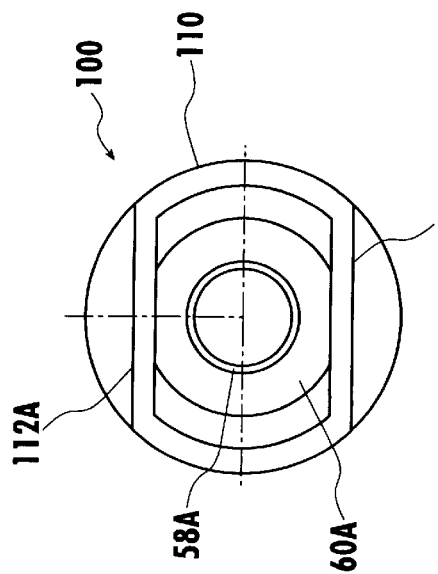
FIG. 21B is a side elevational view of the cap of the present invention rotated 90° relative to FIG. 21A.
Figure 22:
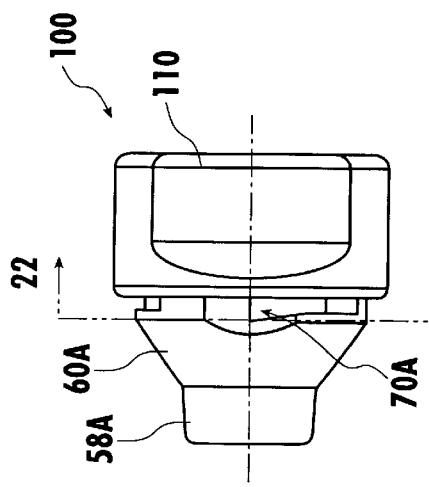
FIG. 22 is a cross-sectional view of the cap of the present invention taken along line 22—22 of FIG. 21A.
Figure 23:
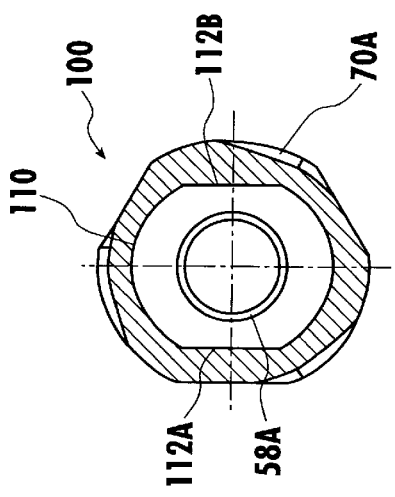
FIG. 23 is a proximal end view of the cap of the present invention.

FIG. 9 illustrates a side view of nozzle 20 showing window 27a and arm portion 24a. In addition spike base 25 can be seen through window 27a. A detail of spike 22 is shown in FIG. 11 to illustrate tip 23, and channel 26. As can be seen in FIG. 10, spike 22 is positioned inwardly from the distal end 21 of adapter 20 so that the possibility of impaling the user's finger or body with spike 22 is minimized.

As shown in FIGS. 4–8, the injector nozzle 50 has an elongated body defining a chamber 52 which communicates with an orifice 54 at the distal end of the nozzle. Fluid such as liquid medicament can pass into the chamber 52 through the orifice 54 in a manner that will be more fully described below during the filling operation. Also fluid can pass out of orifice 54 during the injection process which is also discussed below.

The body of the nozzle 50 is generally cylindrical and at its distal end has a conical tip 56 with orifice 54 positioned centrally in tip 56 along the longitudinal axis X—X of nozzle 50 as shown in FIG. 5. A cylindrical collar 58 extends proximally from the back or rear end of conical tip 56. Following the collar 58 in the proximal direction is a transition portion 60, a flange portion 62 and a cylindrical member 64. As best illustrated in FIG. 4, the nozzle 50 includes a rim 57 positioned between the conical tip 56 and collar 58. When the nozzle is placed within the adapter, rim 57 deforms flexible membrane 61 and provides a sealing function to prevent air or contaminants from approaching nozzle orifice 54. The flange portion 62 has a larger circumference than the collar 58 while the transition portion 60 preferably has increasing cross sections from the collar 58 to the flange 62. A proximal coupler portion 66 is connected to the cylindrical member 64 by a stepped down neck portion 68 as shown in FIGS. 4 and 5. The coupler 66 includes engagement elements such as threads (not shown) which provide for selectively coupling the nozzle 50 to an injector 10 as shown in FIG. 1.

According to a preferred embodiment of the present invention, the nozzle structure discussed above including elements 54 and 56–68 are formed integrally of metal and preferably stainless steel. However, if desired, other materials can be used. As described above with regard to FIG. 2, a plastic nozzle 51 can be used when a disposable component is desired.

Referring to the transition portion 60 of the body of nozzle 50, preferably three depressions 70 are symmetrically or uniformly disposed as shown in FIG. 6 about the longitudinal axis X—X and adjacent the flange 62 proximally from the orifice 54. These depressions 70 are configured so as to receive tabs 34 that can engage the depressions 70 and positively lock the nozzle 50 to the adapter 20. Such locking enables a user such as a medical personnel or even a patient requiring medication to be certain that the nozzle 50 is securely or properly fastened to the adapter to allow for the filling of chamber 52 with the desired medication.

As shown more clearly in FIG. 7, each depression 70 includes an entry region 72, a seating region or portion 74 and an intermediate region 76. The entry region 72 extends circumferentially about the axis X—X from edge 78 along arc 80 which ends at 82. The seating portion 74 extends from 84 to 86.

The surfaces on the transition portion 60 which define the entry and seating regions 72 and 74 are generally flat as shown in FIG. 7. The surface of the intermediate region 76 defined distally by the edge between 82 and 84 and laterally between longitudinal edges 88 and 90 is generally curved with a radius which defines the surface of cylindrical member 64. Therefore, if flange portion 62 were to be removed intermediate region 76 would extend smoothly proximally into cylindrical member 64. The curved surface of region 76 is therefore also defined by the longitudinal edges 88 and 90 and generally circumferential edge 92 as shown in FIG. 7. The edge 83A between 82 and 84 is sloped rearwardly or proximally so that 84 is closer to flange 62 than is 82. Because the outer surface of transition portion 60 has increasing cross sections, a ledge 96 is formed at least under edges 83a and 98, and helps to retain tab 34 after it passes thereunder following rotation through entry portion 72. To further aid in positively locking tab 34 within seating region 74, the distal edge 98 is spaced farther from flange 62 than is edge 83a.

The depressions 70 are dimensioned to engage in a cooperative manner with tab 34 as more fully discussed above to provide for a positive locking of the nozzle 50 or 51 to the adapter 20. Although three depressions 70 are shown in the preferred embodiment illustrated in the drawings and described herein, it is believed sufficient for the present invention that only one depression 70 may be utilized, if desired. Accordingly, only one corresponding tab 34 would be utilized on the adapter 20.

FIG. 20 illustrates the nozzle 50 engaged with the adapter 20 for filling nozzle chamber 52 with liquid medicament. In this position, nozzle tip 56 engages cup 55 with central ring 69 of flexible membrane 61 pressed therebetween. In addition, nozzle rim 57 compresses intermediate ring 65 to provide additional sealing protection between the fluid path and the external nozzle portions. The compressed areear is shown as bulge 55 in FIG. 20. Thus, fluid can be withdrawn from the medicament container through channel 26 of spike 22 and thereafter through wall passageway 28, membrane passageway 95 and nozzle orifice 54 into nozzle chamber 52. This is achieved by the alignment of the apertures and the withdrawal of the plunger mechanism 14.

After disconnection from adapter 20, injector 10 is ready to administer the medicament to a subject by expelling the medicament from the chamber 52 and through the nozzle orifice 54 by the action of a ram or piston which drives the plunger assembly at high speed through the chamber.

With reference to FIGS. 21A to 23, there is shown a cap 100 which has a generally cylindrical elongated body that generally conforms to the shape of the distal end of nozzle 50, 51 and can be used to couple to adapter 20 when the nozzle 50, 51 is removed as shown in FIG. 3B. The cap 100 has a distal end 58A that is configured to seat within membrane retainer 71. However, unlike nozzle 50, cap 100 does not have a conical tip portion or aperture since the cap 100 serves a sealing function for the medicament container by blocking flexible membrane 61, aperture 95 and wall opening 28. Without a conical tip, cap 100 does not unnecessarily stretch membrane 61.

Like nozzle 50, cap 100 has a transition portion 60A with corresponding depressions 70a that can engage tab member 34 and retain the cap 100 to the adapter 20. The cap 100 has a proximal portion 110 which has two gripping flats 112A, 112B to facilitate grasping by the user for ease in attachment of cap 100 to adapter 20.

What is claimed is:

1. An injector nozzle comprising a body defining a chamber, with a portion of the body having an orifice communicating with the chamber for allowing fluid to enter into or exit from the chamber; said body portion including at least one depression comprising an entry portion and a seating portion which are positioned in spaced relation by an intermediate portion; said depression configured and dimensioned to cooperatively engage with a tab member of an associated component for coupling thereto; said depression further configured and dimensioned to positively lock the body portion to the associated component wherein the intermediate portion is narrower in width than the seating portion to provide positive feedback when said tab member engages the seating portion.

2. The nozzle of claim 1, wherein the body portion containing the depression is spaced proximally from the nozzle orifice, and at least two depressions are present, with the depressions being uniformly disposed with respect to the orifice.

3. The nozzle of claim 1, wherein the at least one depression has a distal edge that varies in slope; a portion of the distal edge includes a ledge; and the entry portion and the seating portion have a flat surface and the intermediate portion has a curved surface.

4. The nozzle of claim 1, wherein the body portion is generally cylindrical and includes a conical tip which surrounds the orifice, a cylindrical collar surrounding the conical tip, a flange portion having a greater circumference than the collar, and a transition portion connecting the collar to the flange portion, wherein the transition portion includes the at least one depression.

5. The nozzle of claim 4, wherein the transition portion includes a transverse cross section of generally increasing size from the cylindrical collar to the flange portion.

6. The nozzle of claim 1, wherein the body further comprises a proximal portion which includes engagement means for selectively coupling said nozzle to an injector.

7. An adapter for coupling a nozzle to a fluid container comprising a tubular member having first and second ends and a wall therebetween; said wall including a passageway therethrough and having an annular rib surrounding said passageway at the first and with the first end and rib being configured and dimensioned to cooperatively engage with an injector nozzle having an orifice such that the nozzle is seated by the rib and wall such that the nozzle orifice substantially aligns with the wall passageway for fluid communication therebetween; and the second end being configured and dimensioned to cooperatively engage with a fluid container.

8. The adapter of claim 7, which further comprises a flexible membrane positioned between the wall and the first end of the tubular member, said membrane including a generally centrally disposed aperture to facilitate fluid communication between the nozzle orifice and the wall passageway; and the rib protrudes from the wall and extends toward the first end of the tubular member for receiving an injector nozzle tip, wherein the surface defined by the rib and the wall has a shape generally conforming to the nozzle tip so that the membrane seals the nozzle orifice to the wall passageway.

9. The adapter of claim 8 further comprising a membrane retainer having a generally annular configuration disposed within the first end of the tubular member for retaining the membrane adjacent the wall.

10. The adapter of claim 7, wherein the first end of the tubular member includes at least one inwardly extending tab portion for engaging a depression on the nozzle.

11. The adapter of claim 10, wherein the first end of the tubular member includes at least two inwardly extending tab portions for engaging corresponding depressions on the nozzle, wherein the tab portions are uniformly disposed along the first end and each tab portion includes a protuberance for slidingly engaging the corresponding depression to positively lock the tubular portion to the nozzle.

12. The adapter of claim 7, wherein the second end of the tubular member includes inwardly extending frangible arm portions for engaging a fluid container.

13. The adapter of claim 12, wherein the tubular member includes a spike which contains a fluid passage therein, said spike extending from the wall toward the second end of the tubular member for penetrating a sealing member of the fluid container.

14. The adapter of claim 7, wherein said rib has a sloped wall for receiving a sloped nozzle.

15. A system for transferring fluid from a fluid container to an injector device which comprises:

an injector nozzle having a body defining a chamber, with a portion of the body having an orifice communicating with the chamber for allowing fluid to enter into or exit from the chamber, said body portion including at least one depression comprising an entry portion and a seating portion which are positioned in spaced relation by an intermediate portion; said depression configured and dimensioned to cooperatively engage with a tab member of an associated component for coupling thereto, said depression further configured and dimensioned to positively lock the body portion to the associated component wherein the intermediate portion is narrower in width than the seating portion to provide positive feedback when said tab member engages the seat portion; and an adapter for coupling the nozzle to a fluid container, comprising a tubular member having first and second ends and a wall therebetween, said wall including a passageway therethrough with the first end configured and dimensioned to cooperatively engage with an injector nozzle having an orifice such that the nozzle orifice generally aligns with the wall passageway for fluid communication therebetween, and the second end being configured and dimensioned to cooperatively engage the fluid container.

16. The system of claim 15, wherein the body portion of the nozzle contains at least two depressions which are uniformly disposed with respect to the orifice and the first end of the adapter contains at least two inwardly extending tab portions uniformly disposed therealong for engaging the depressions.

17. The system of claim 15, wherein the nozzle includes a conical tip which surrounds the orifice, a cylindrical collar surrounding the tip, a flange portion having a greater circumference than the collar, and a transition portion connecting the collar to the flange portion, wherein the transition portion includes the at least one depression; the adapter includes a flexible membrane positioned between the wall and the first end of the tubular member, said membrane including a generally centrally disposed aperture to facilitate fluid communication between the nozzle orifice and the wall passageway; and a rib protruding from the wall and extending toward the first end of the tubular member for receiving the injector nozzle tip, wherein the surface defined by the rib and the wall has a shape generally conforming to the nozzle tip so that the membrane seals the nozzle orifice to the wall passageway.

18. The system of claim 17, wherein the adapter further comprises a membrane retainer having a generally annular configuration disposed within the first end of the tubular member for retaining the membrane adjacent the wall and the collar member of the nozzle contacts the membrane and engages the inner surface of the retainer to align the nozzle orifice with the wall passageway with the membrane acting as a seal to prevent air from entering the nozzle orifice.

19. The system of claim 17, wherein the flexible membrane includes an inner portion and an outer portion, said inner portion including the generally centrally disposed aperture and having a first thickness and being dimensioned and configured for receiving the conical tip of the nozzle; and said outer portion having a second thickness which is greater than the first thickness.

20. The system of claim 15, wherein the second end of the tubular member includes inwardly extending frangible arm portions for engaging the fluid container; and a spike which contains a fluid passage therein extending from the wall toward the second end of the tubular member for penetrating a sealing member of the fluid container.

21. The system of claim 15, wherein the nozzle body further comprises a proximal portion which includes engagement means for selectively coupling the nozzle to an injector.

22. A system for transferring fluid from a fluid container to an injector device which comprises:

an injector nozzle having a body defining a chamber, with a portion of the body having an orifice communicating with the chamber for allowing fluid to enter into or exit from the chamber, said body portion including at least one depression configured and dimensioned to cooperatively engage with a tab member of an associated component for coupling thereto, said depression further configured and dimensioned to positively lock the body portion to the associated component; an adapter for coupling the nozzle to a fluid container, comprising a tubular member having first and second ends and a wall therebetween, said wall including a passageway therethrough with the first end being configured and dimensioned to cooperatively engage with an injector nozzle having an orifice such that the nozzle orifice generally aligns with the wall passageway for fluid communication therebetween, and the second end being configured and dimensioned to cooperatively engage with the fluid container; and a cap having a body for coupling to the adapter when the nozzle is removed therefrom, said cap defining a first body portion which is configured and dimensioned to couple with the first end of the adapter to block the transmission of fluid through the wall passageway, said first body portion including at least one groove configured and dimensioned to cooperatively engage with the tab member of the adapter, and a second body portion including an extending member for seating the cap within the first end of the adapter and for removing the cap therefrom.

* * * * *

UNITED STATES PATENT AND TRADEMARK OFFICE
CERTIFICATE OF CORRECTION

PATENT NO. : 5,769,138

DATED : June 23, 1998

INVENTORS : SADOWSKI et al.

It is certified that error appears in the above-identified patent and that said Letters Patent is hereby corrected as shown below:

Column 10, line 14: change the first occurrence of "and" to --end--.

Column 11, line 6: change "seat" to --seating--.

Signed and Sealed this

Eighteenth Day of August, 1998

*Attest:*

BRUCE LEHMAN

*Attesting Officer*    *Commissioner of Patents and Trademarks*